United States Patent [19]

Fujii et al.

[11] Patent Number: 4,490,388
[45] Date of Patent: Dec. 25, 1984

[54] AMIDINE COMPOUND AND ANTICOMPLEMENT AGENT COMPRISING SAME

[75] Inventors: Setsuro Fujii, Toyonaka; Takuo Aoyama, Sakura; Yojiro Sakurai, Kamakura; Toyoo Nakayama, Funabashi; Shigeki Nunomura, Chiba; Takashi Yaegashi, Funabashi; Toshiyuki Okutome, Tokyo, all of Japan

[73] Assignee: Torii & Co., Ltd., Tokyo, Japan

[21] Appl. No.: 350,964

[22] Filed: Feb. 22, 1982

[30] Foreign Application Priority Data

Feb. 27, 1981 [JP] Japan .................................. 56-27973
Sep. 18, 1981 [JP] Japan ................................. 56-147289

[51] Int. Cl.³ .................... C07C 101/00; A61K 31/215
[52] U.S. Cl. ..................................... 424/278; 424/304; 424/309; 424/310; 424/311; 424/314; 260/465 D; 549/436; 549/438; 560/1; 560/18; 560/20; 560/24; 560/27; 560/34; 560/49; 560/51; 560/64; 560/72; 560/86; 560/104; 560/105; 560/109; 560/122; 560/123; 560/124; 560/125; 560/126; 560/127; 560/128
[58] Field of Search ................. 560/34, 142, 110, 121, 560/123, 124, 1, 18, 20, 27, 24, 49, 51, 64, 72, 86, 104, 105, 109, 122, 125, 126, 127, 128; 424/330, 278, 304, 309, 310, 311, 314; 549/436, 438; 260/465 D

[56] References Cited

U.S. PATENT DOCUMENTS 3,579,510  5/1971  McFarland ..................... 560/142 X
4,021,472  5/1977  Fujii et al. ............................ 560/34
4,224,342  9/1980  Fujii et al. ....................... 560/34 X

*Primary Examiner*—Bernard Helfin
*Attorney, Agent, or Firm*—Beveridge, DeGrandi & Kline

[57] ABSTRACT

Amidino compounds represented by the formula (I)

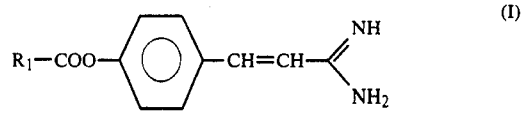

and pharmaceutically acceptable acid addition salts thereof are novel compounds and are useful as powerful antitrypsine, antiplasmin, antikallikrein and anti-thrombin agents. Having strong anti-Cl ($\overline{Clr}$, $\overline{Cls}$) activities and an anticomplement activity, they are also useful as anticomplement agents. These amidino compounds are prepared by usual esterification of carboxylic acid compounds represented by the formula (II)

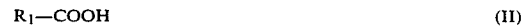

with 4-(β-amidinoethenyl)phenol represented by the formula (III)

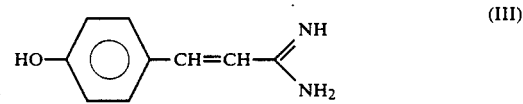

and, if necessary, can be transformed into pharmaceutically acceptable acid addition salts thereof.

11 Claims, No Drawings

AMIDINE COMPOUND AND ANTICOMPLEMENT AGENT COMPRISING SAME

This invention relates to amidino compounds (I) of the formula

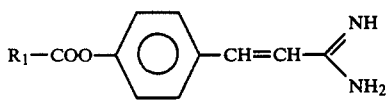

(I)

having strong anti-trypsin, anti-plasmin, anti-kallikrein and anti-thrombin activities and also an anti-complement activity, and to a process for producing said novel compounds.

Leupeptin is known to be a substance having an anti-complement activity [Y. Takada et al., Immunology 34, 509-515 (1978)]. The present compound (I) has anti-complement activity stronger than that of Leupeptin. This means that with respect to anti-complement activities, the same pharmaceutical effect is obtained with a smaller dose of the compound (I) than with a dose of leupeptin.

An object of this invention is to provide a pharmaceutically useful amidino compounds represented by the formula (I)

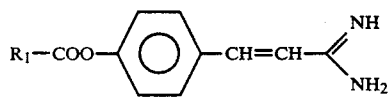

(I)

and pharmaceutically acceptable acid addition salts thereof.

Another object of this invention is to provide powerful anti-trypsin, anti-plasmin, anti-kallikrein and anti-thrombin agents.

A still another object of this invention is to provide powerful anti-complement agents.

A further object of this invention is to provide a process for producing said amidino compounds.

The present compound (I) can be produced by subjecting a carboxylic acid compound represented by the following formula (II) or a reactive intermediate thereof and 4-(β-amidinoethenyl)phenol of the following formula (III) to usual esterification:

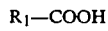

(II)

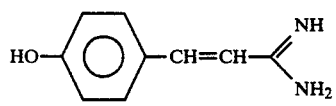

(III)

This invention relates to an amidino compound represented by the formula (I)

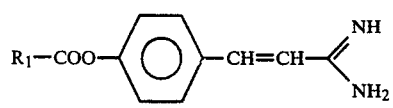

(I)

In formulas of the amidino compound (I) and the carboxylic acid compound (II) described in this Specification and the appended Claims, $R_1$ represents a straight or branched chain alkyl group of 1 to 6 carbon atoms, a straight or branched chain alkenyl group possessing 1 to 3 double bonds of 2 to 6 carbon atoms, a cycloalkyl group of 3 to 6 carbon atoms, a cycloalkenyl group possessing 1 to 2 double bonds of 3 to 6 carbon atoms, $R_2-(CH_2)_a-$,

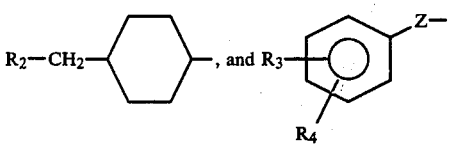

[where a is 1, 2, 3, 4 or 5, $R_2$ is an amino group or guanidino group, or amino group or guanidino group possessing amino or guanidino protecting group, $R_3$ and $R_4$, which may be the same or different, represent each a hydrogen atom, straight or branched chain alkyl group of 1 to 4 carbon atoms,

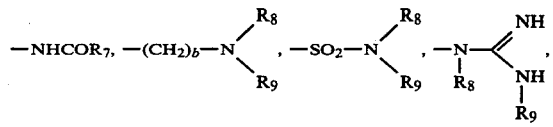

$NO_2$, CN, halogen, $CF_3$, or methylenedioxy (where b is 0, 1 or 2; $R_5$ is a hydrogen atom, a straight or branched chain alkyl group of 1 to 4 carbon atoms, or benzyl group; $R_6$ is a hydrogen atom or a straight or branched chain alkyl group of 1 to 4 carbon atoms; $R_7$ is a straight or branched chain alkyl group of 1 to 4 carbon atoms; and $R_8$ and $R_9$, which may be the same or different, are each a hydrogen atom, a straight or branched chain alkyl group of 1 to 4 carbon atoms, or amino protecting group), Z represents $-(CH_2)_c-$,

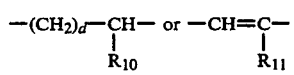

(where c is 0, 1, 2 or 3, d is 0, 1 or 2, $R_{10}$ is a straight or branched chain alkyl group of 1 to 4 carbon atoms, and $R_{11}$ is a hydrogen atom or a straight or branched chain alkyl group of 1 to 4 carbon atoms)].

The straight or branched chain alkyl groups of 1 to 4 carbon atoms are $CH_3$, $C_2H_5$, $n-C_3H_7$, $i-C_3H_7$, $n-C_4H_9$, $i-C_4H_9$, $sec-C_4H_9$ and $t-C_4H_9$.

Examples of the straight or branched chain alkyl groups of 1 to 6 carbon atoms include $CH_3$, $C_2H_5$, $n-C_3H_7$, $i-C_3H_7$, $n-C_4H_9$, $i-C_4H_9$, $sec-C_4H_9$, $t-C_4H_9$, $n-C_5H_{11}$ and $n-C_6H_{13}$.

Examples of the straight or branched chain alkenyl groups of 2 to 6 carbon atoms possessing 1 to 3 double bonds include $CH_2=CH-$, $CH_3CH=CH-$, $CH_2=CH-CH=CH-$, $CH_3-CH=CH-CH_2-$,

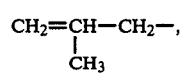

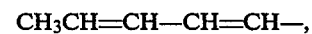

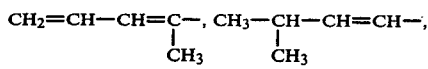

and CH₂=CH—CH=CH—CH=CH—.

Examples of the cycloalkyl groups of 3 to 6 carbon atoms or cycloalkenyl groups possessing 1 or 2 double bonds of 3 to 6 carbon atoms include

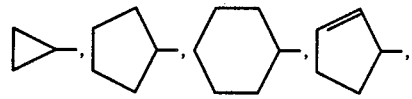

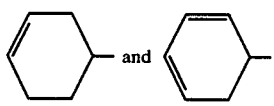

Examples of the protecting groups for the amino or guanidino radical include t-butyloxycarbonyl group, benzyloxycarbonyl group, acetyl group, benzoyl group, tosyl group and nitro group.

Therefore, examples of $R_1$ are CH₃—, C₂H₅—, n—C₃H₉—, i—C₃H₇—, n—C₄H₉—, i—C₄H₉—, sec—C₄H₉—, t—C₄H₉—, n—C₅H₁₁—, n—C₆H₁₃—, CH₂=CH—, CH₃CH=CH—, CH₂=CH—CH=CH—, CH₃—CH=CH—CH₂—, $$CH_2=C-CH_2-, \atop CH_3$$

CH₃CH=CH—CH=CH—, $$CH_2=CH-CH=C-, \ CH_3-CH-CH=CH, \atop CH_3 \quad\quad CH_3$$

CH₂=CH—CH=CH—CH=CH—,

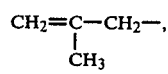

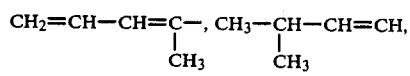

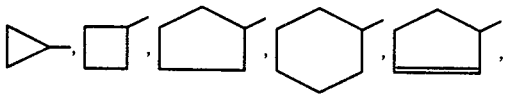

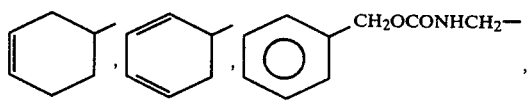

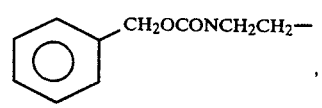, H₂NCH₂—, H₂NCH₂CH₂—,

-continued

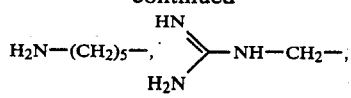

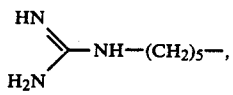

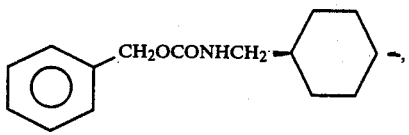

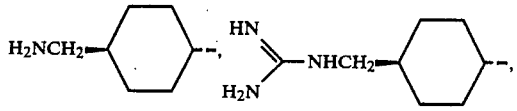

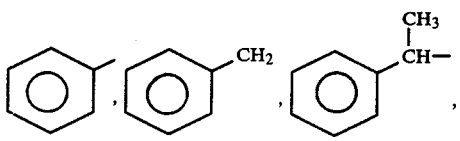

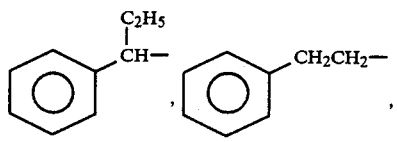

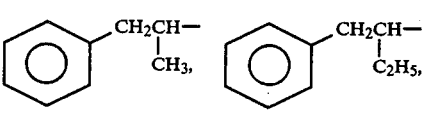

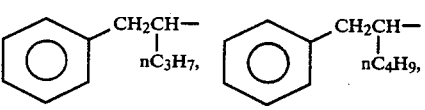

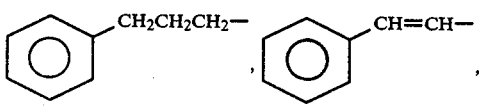

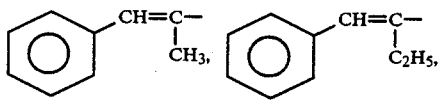

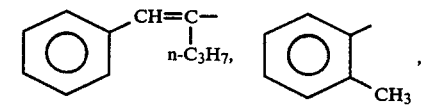

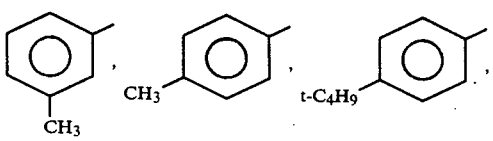

-continued
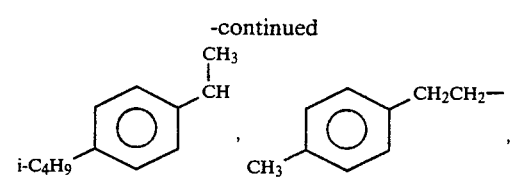
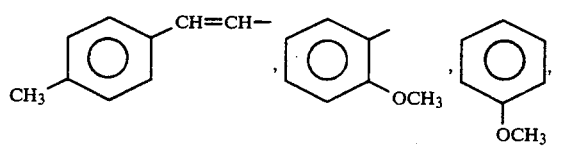
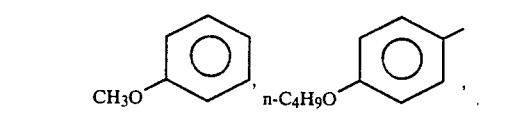
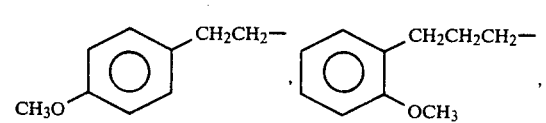
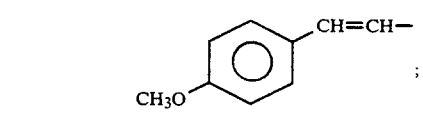
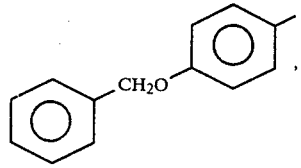
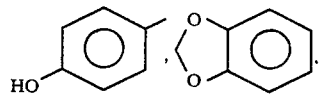
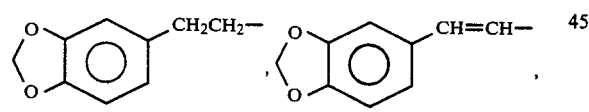
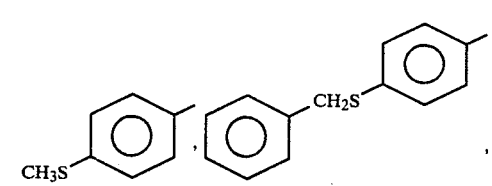
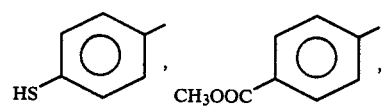
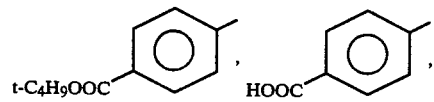
-continued
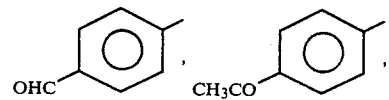
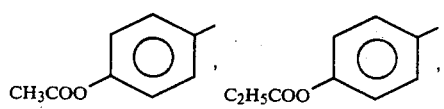
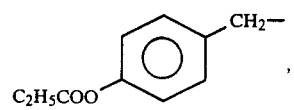
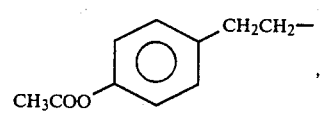
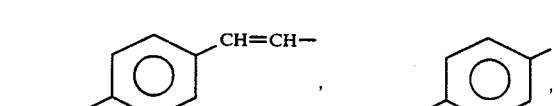
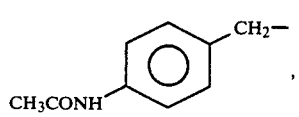
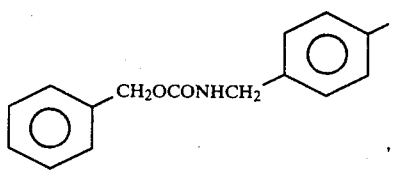
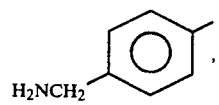
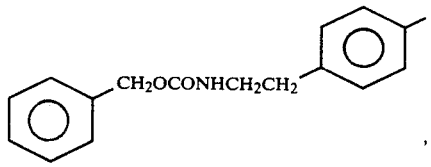
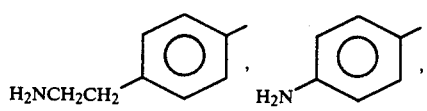
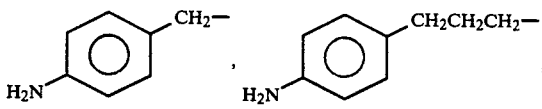

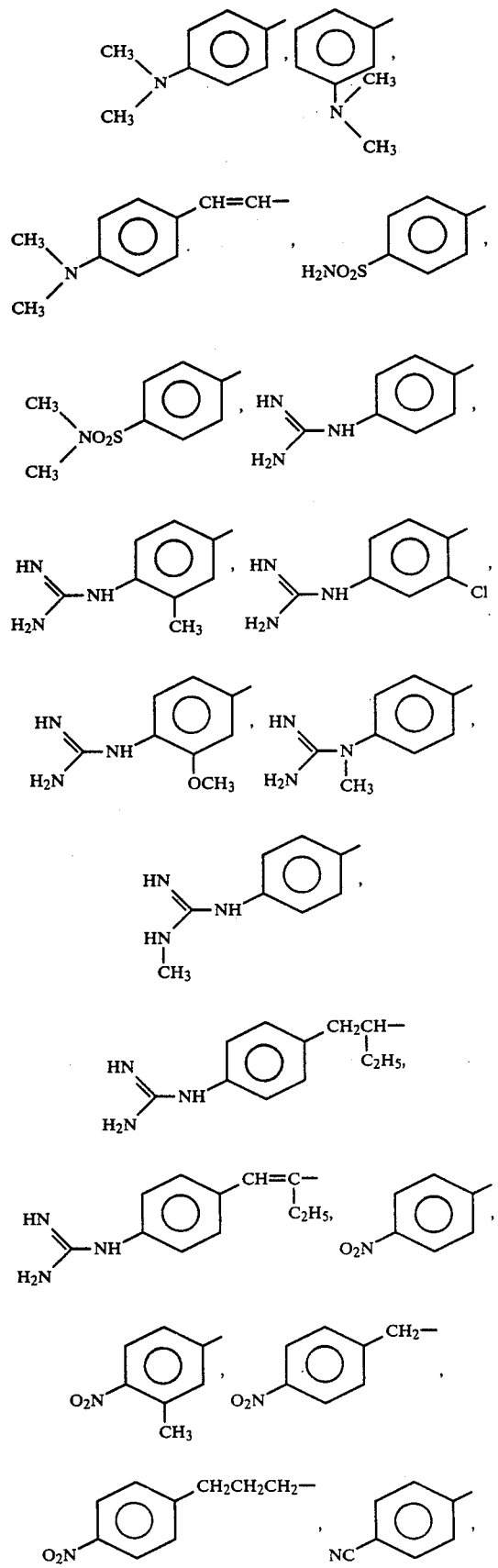

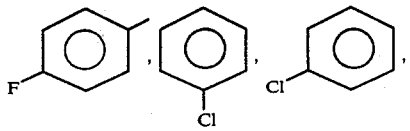

The compound (I) of this invention can be produced by the reaction between a carboxylic acid compound of the formula (II) or a reactive intermediate thereof and 4-(β-amidinoethenyl)phenol of the formula (III) or preferably an acid addition salt thereof. The reactive intermediates, as herein referred to, include acid halides and acid anhydrides commonly used in the dehydration condensation and the reactive intermediates formed by reacting dicyclohexyl carbodiimide (DCC), diphenylphosphorylazide (DPPA), or the like with a carboxylic acid derivative.

The process for producing the present compound is described below in detail.

The present compound (I) can be prepared by dissolving or suspending a carboxylic acid compound (II) in an organic solvent such as dimethylformamide, pyridine, then allowing the compound (II) to react with a carboxylic acid activator such as dicyclohexylcarbodiimide (DCC), diphenylphosphoryl azide (DPPA), which is usually used as dehydration-condensation agent, and adding 4-(β-amidinoethenyl)phenol (III) or preferably an acid addition salt thereof to the reaction product.

For instance, when DCC is used as the dehydration-condensation agent, a carboxylic acid derivative (II) is added to a solvent such as pyridine, then the mixture is stirred with cooling in ice or at room temperature for 10 minutes to 2 hours, then 4-(β-amidinoethenyl)phenol (III) is added, and the mixture is further stirred at a temperature between −30° and 80° C., preferably at room temperature, for 3 to 5 hours to complete the reaction, though it is not objectionable to continue the reaction overnight. Dicyclohexylurea (DCU) precipitates out of the reaction mixture, while the present compound (I) either precipitates with DCU or remains dissolved in the solvent. In the former case, both precipitates are collected by filtration, then suspended in a suitable solvent such as dimethylformamide or the like and the mixture is filtered to remove insoluble DCU. After adding to the filtrate a solvent such as ethyl ether, ethyl acetate, acetone or the like, the precipitate is collected by filtration to obtain the present compound (I). Alternatively, the combined precipitate of DCU and the present compound (I) is collected by filtration, then added to a suitable solvent such as dimethylformamide, water or the like to remove insoluble DCU by filtration, the filtrate is added to a saturated aqueous sodium bicarbonate solution to obtain the present compound (I) in the form of carbonate. In the latter case, where the present compound remains dissolved in the reaction mixture, DCU is removed by filtration and the filtrate is admixed with a solvent such as ethyl ether, acetone, ethyl acetate, to obtain the present compound (I).

In another process, when it is inteded to use an acid halide as a reactive intermediate of a carboxylic acid derivative (II), the latter derivative (II) is allowed to react with an acid halogenation agent such as $SOCl_2$, $SOBr_2$, $PCl_5$ to synthesize an acid halide represented by the formula (IV)

$$R_1-COX \qquad (IV)$$

wherein $R_1$ is as defined above and X represents a halogen atom. The acid halide is added to a solution of 4-(β-amidinoethenyl)phenol (III), preferably in the form of an acid addition salt, dissolved in dimethylformamide, pyridine, dimethyl sulfoxide and allows to react in the presence of a dehydrohalogenation agent. The dehydrohalogenation agents which can be used include inorganic bases such as potassium carbonate, sodium carbonate, sodium hydroxide and the like and organic bases such as triethylamine, pyridine, dimethylaniline. Of these bases, pyridine is preferred. Although the reaction proceeds readily at a temperature in the range of −30° to 80° C., it is preferable for the purpose of avoiding side reactions to conduct the reaction in the early stage under ice cooling and then at room temperature. The reaction is complete in 2 to 5 hours, though the reaction mixture can be left overnight. After completion of the reaction, the reaction mixture is treated in a customary manner. For instance, when pyridine was used as the reaction medium, a solvent such as ethyl ether or ethyl acetate is added to the reaction mixture to precipitate a solid reaction product which is then recrystallized from a suitable solvent such as a methanol-ethyl ether mixture to obtain the present compound (I).

Further, if desired, the present compound (I) can be prepared in the corresponding reduced form by the reduction of a suitable compound of formula (I) by use of a suitable reducing agent. For example, a compound of formula (I) having a nitro group is converted into a compound of formula (I) having an amino group by the reduction. It is also possible to convert a cinnamic acid ester derivative having a double bond into a phenylpropionic acid derivative.

Still further, if desired, the present compound can be obtained by the removal of protective groups of amino, hydroxyl, and carboxyl groups. The protective groups, as herein referred to, include those which are commonly used, such as, for example, benzyloxycarbonyl, tert-butoxycarbonyl, benzyl and tert-butyl groups. For instance, a compound having an aminomethyl group is obtained by the removal of the protective group from a compound having a benzyloxycarbonylaminomethyl group and a compound having a hydroxy group is obtained from a compound having a benzyloxy group.

If necessary, acid addition salts of the present compound may be prepared in a customary manner. For instance, carbonate of the present compound is dissolved or suspended in a solvent such as methanol, DMF and the carbonate is allowed to dissolve by the addition of an acid such as methanesulfonic acid, hydrochloric acid. To the resulting solution is added a solvent such as ethyl ether, ethyl acetate to obtain a corresponding acid addition salt. Acids which can be used are pharmaceutically acceptable ones including inorganic acids such as hydrochloric acid, sulfuric acid and phosphoric acid and organic acids such as acetic acid, lactic acid, citric acid, methanesulfonic acid, succinic acid, fumaric acid and maleic acid.

The 4-(β-amidinoethenyl)phenol (III) employed as a starting material in synthesizing the compounds of this invention is a novel compound and is useful as a starting material in synthesizing the compounds of this invention.

A method for the synthesis of 4-(β-amidinoethenyl)-phenol (III) used as a starting material is shown below. However, the method shown below is merely an example and not limitative.

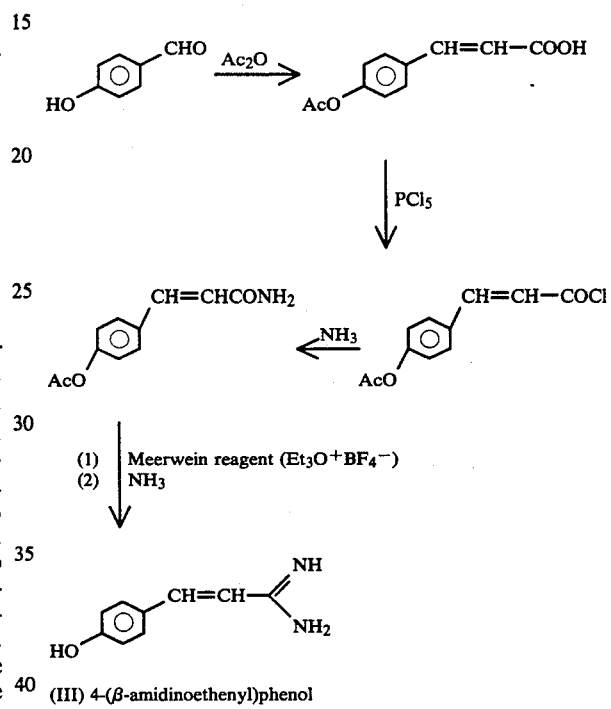

(III) 4-(β-amidinoethenyl)phenol

The present compound and the pharmaceutically acceptable acid addition salt thereof possess powerful inhibitory activities against proteases, that is, trypsin, plasmin, kallikrein and thrombin and are effective as an anti-trypsin agent for the treatment of pancreatitis, as an anti-plasmin or anti-kallikrein agent for hemorrhagic diseases, and as an anti-thrombin agent for thrombus.

With respect to the above-mentioned proteases, their roles in a living body, the relationship to the diseases, the clinical significance of these protease inhibitors and the significance of the tests herein performed are explained below:

I. Trypsin: Trypsin is a protease existing originally in the form of proenzyme trypsinogen in the pancrease and the proenzyme is secreted into the small intestine where it is transformed into trypsin by activation with enterokinase existing therein. Trypsin has a role as one of digestive enzymes. If the trypsinogen is activated by any chance in the pancreas to form tryspin, the pancreas tissue will be injured to manifest clinically the symptoms of pancreatitis. In fact, it is known that in an experiment using rat as test animal, when trypsin is injected conversely into the pancreas, the onset of intense pancreatitis is observed but the disease is cured by the administration of a trypsin inhibitor. From this fact, it is presumable that the present compound having a strong trypsin inhibitory activity is useful as an anti-trypsin agent which is clinically effective for the treatment of pancreatitis.

II. Plasmin: Plasmin is an enzyme existing in the blood, usually in the form of proenzyme plasminogen which is converted to plasmin by the activation with a plasminogen tissue activator such as urokinase. This enzyme acts reversely to the action of thrombin, that is, it acts to dissolve fibrin. For this reason, plasmin plays an important role in securing blood flow through capillaries. However, when this enzyme becomes abnormally activated for some reason, it causes hemorrhagic diseases. This enzyme participates also in inflammation, increasing the vascular permeability and causing edema or the like. Therefore, an inhibitor for this enzyme is useful as a drug to treat hemorrhagic diseases and inflammation.

III. Kallikrein: Kallikrein is an enzyme widely distributed in blood and other organs and glands, usually in the form of its precursor prekallikrein which is activated with Hageman factor or other proteases. This enzyme participates in the hypotensive kallikrein-kinin system which counteracts the hyper tensive reninangiotensin system and plays an important role in the control of blood pressure. This enzyme participates also in exogenous coagulation system. Further, kallikrein originated from organs or glands plays an important role in the improvement of local circulation. However, an abnormal activation, particularly an abnormal local activation, of this enzyme causes an insufficiency of local circulation due to the exaggeration of coagulation system, causing inflammation, ulcer, or the like. Therefore, a kallikrein inhibitor is useful for the control of blood pressure and as a drug for the treatment of inflammation or ulcer.

IV. Thrombin: Thrombin is known as an enzyme having a blood coagulating activity. In normal state, thrombin is formed by the activation of prothrombin in the blood when the vascular wall is injured. Thrombin acts to decompose the fibrinogen in the blood into fibrin. The resulting fibrin deposits on the injured part of vascular wall to prevent plasma components from transdation and simultaneously to promote the restoration of tissues. However, when the coagulation system is abnormally activated for some reason, a large number of fine thrombic are formed in capillaries throughout the entire body. Therefore, the present compound is useful as a drug for the treatment of such a disease.

The present compound and its pharmaceutically acceptable acid addition salts possess a strong C1 esterase (C1r̄, C1s̄) inhibitory activity, an ability of inhibiting the complement mediated hemolysis, and a therapeutic activity against the Forssman shock in which the activation of the complement system caused by an immune complex is said to play an important role. This indicates that the present compound is useful as an anticomplement agent effective for the treatment of allergic diseases such as nephritis associated with the complement.

The role of complement in the living body, the interrelation between a disease and the complement, the clinical significance of inhibitor, and the significance of tests (inhibition of C1r̄, C1s̄, complement mediated hemolysis, and Forssman shock) performed by the present inventors are described below.

Anti-complement activity:
(1) C1r̄, C1s̄
The complement is one of the serum components and comprises 9 components of C1 to C9. C1 is separated into 3 subcomponents of C1q, C1r̄ and C1s̄. C1s̄ and C1r̄ mean activated C1s and activated C1r, respectively. The complement was thought at first to perform a part of the infection protective process of living body, since it shows bacteriolysis, but recently an intimate relation to the immunity has been evident. It was shown that the complement is activated by the immune complex progressively from C1 to C9 and exhibits cytolysis or hemolysis at the final stage (activation of C9). It was also disclosed that the fragments (e.g. C3a, C5a) liberated in the course of activation of the complement system exaggerate the vascular permeability and promote the chemotaxis of polymorphonuclear leucocytes or immune adherence. Since that time, the interrelationship between the abnormal activation of complement and various diseases, particularly immune diseases, has been extensively investigated and, as the result, the intimate association of autoimmune diseases with the complement is beginning to be disclosed. Examples of autoimmune diseases caused by the abnormal activation of complement include autoimmune hemolytic anemia, autoimmune thrombocytopenia, leukopenia, glomerulonephritis, systemic lupus erythematosus, serum sickness and periarteritis nodosa. It is expectable to cure such diseases by inhibiting the activation of complement or inhibiting the activated complement in an early stage. The present inventors examined the C1 esterase inhibitory effect of the present compound by using C1 esterase as target enzyme and, in addition, the influence of the present compound on the complement system to estimate the usefulness of the present compound as a drug for the treatment of autoimmune diseases.

(2) Complement mediated hemolysis:
The complement mediated hemolysis is widely used as a means to determine the titration of complement. The principle of this method is based on the fact that hemolysis is caused by the activation of complement, when the latter is added to a complex (immune complex) of erythrocytes and the autibody thereof. The degree of hemolysis varies in proportion to the amount of complement added. Therefore, when a known amount of complement admixed with a C1 esterase inhibitor is used, the hemolysis must be suppressed in proportion to the inhibitory activity. The present compound having C1 esterase inhibitory activity showed strong inhibition of complement mediated hemolysis as shown hereinafter.

(3) Forssman shock:
Quite different from other animals, guinea pig has on the surface of its organs a specific antigen called Forssman antigen which specifically reacts with the antibody of sheep erythrocyte. Forssman shock is based on the above principle and is a shock caused by the administration of antibody of sheep erythrocyte to a guinea pig. The Forssman shock was investigated in detail by many researches and it was definitely shown that this shock is a model case where the complement plays the principal part and that the shock is associated with a classical pathway in which the complement system is activated progressively starting from C1. Since the participation of complement in autoimmune diseases has been established, the Forssman shock can be said to be a useful means for testing a drug for autoimmune diseases. A drug effective for the treatment of Forssman shock is useful as a drug of autoimmune diseases. [Anti-trypsin, anti-plasmin, anti-kallikrein and anti-thrombin activities]

The anti-trypsin, anti-plasmin, anti-kallikrein and anti-thrombin activities were determined according to the method of Muramatsu et al. [M. Muramatsu, T. Onishi, S. Makino, Y. Hayashi and S. Fujii, J. of Biochem., 58, 214 (1965)]. The results were as shown in Table 1. The data summarized in Table 1 are expressed in terms of molar concentration (id$_{50}$) of the test compound which inhibits 50% of the activity of each enzyme to hydrolyze TAME (tosylarginine methyl ester). The compound No. corresponds to the compound number shown in Examples. The figure in parentheses shows the percentage inhibition at a concentration of the compound of $1 \times 10^{-5}$M.

TABLE 1

| Compound No. | Trypsin | Plasmin | Thrombin |
|---|---|---|---|
| 3 | >10$^{-5}$ | >10$^{-5}$ | >10$^{-5}$ |
| 4 | 4 × 10$^{-7}$ | 9 × 10$^{-7}$ | |
| 5 | 6 × 10$^{-6}$ | | 2 × 10$^{-6}$ |
| 7 | 7 × 10$^{-6}$ | 5 × 10$^{-6}$ | >10$^{-5}$ |
| 8 | 2 × 10$^{-6}$ | >10$^{-5}$ | >10$^{-5}$ |
| 9 | 3 × 10$^{-8}$ | >10$^{-5}$ | >10$^{-5}$ |
| 10 | 6 × 10$^{-6}$ | 6 × 10$^{-6}$ | >10$^{-5}$ |
| 11 | 5 × 10$^{-6}$ | 3 × 10$^{-7}$ | >10$^{-5}$ |
| 12 | 6 × 10$^{-7}$ | 2 × 10$^{-6}$ | 3 × 10$^{-6}$ |
| 13 | 1 × 10$^{-6}$ | 1 × 10$^{-5}$ | 5 × 10$^{-6}$ |
| 14 | 9 × 10$^{-6}$ | 8 × 10$^{-6}$ | 8 × 10$^{-6}$ |
| 15 | 2 × 10$^{-6}$ | >10$^{-5}$ | >10$^{-5}$ |
| 20 | 3 × 10$^{-8}$ | 4 × 10$^{-6}$ | >10$^{-5}$ |
| 22 | 5 × 10$^{-6}$ | 3 × 10$^{-6}$ | 3 × 10$^{-6}$ |
| 26 | 2 × 10$^{-7}$ | >10$^{-5}$ | >10$^{-5}$ |
| 28 | 26 | 1 × 10$^{-6}$ | 3 × 10$^{-6}$ |
| 30 | 4 × 10$^{-6}$ | 6 × 10$^{-7}$ | 6 × 10$^{-7}$ |
| 32 | 1 × 10$^{-6}$ | >10$^{-5}$ | >10$^{-5}$ |
| 35 | 2 × 10$^{-8}$ | 9 × 10$^{-7}$ | 1 × 10$^{-6}$ |

TABLE 1-continued

| Compound No. | Trypsin | Plasmin | Thrombin |
|---|---|---|---|
| 36 | 5 × 10$^{-6}$ | >10$^{-5}$ | 5 × 10$^{-6}$ |
| 39 | 2 × 10$^{-6}$ | 4 × 10$^{-6}$ | 2 × 10$^{-6}$ |
| 41 | 3 × 10$^{-6}$ | 3 × 10$^{-6}$ | >10$^{-5}$ |

[Anti-complement activity]

(1) Anti-C1 (C1r̄, C1s̄) activity and inhibition of complement mediated hemolysis:

The anti-C1 esterase (C1r̄, C1s̄) activity was determined according to the method of Okamura et al. [K. Okamura, M. Muramatsu and B. Fujii, Biochem. Biophys. Acta, 295, 252–257 (1973)]. The inhibition of complement mediated hemolysis was determined according to the method of Baker et al. [B. R. Baker and E. H. Erickson, J. Med. Chem., 12, 408–414 (1969)]. The results obtained were as shown in Table 2. The figures in Table 2 have the following meanings:

C1r̄: Molar concentration of the test compound which inhibits 50% of the ability of C1r̄ to hydrolyse AAME (acetylarginin methyl ester) (id$_{50}$).

C1s̄: Molar concentration of the test compound which inhibits 50% of the ability of C1s̄ to hydrolyse ATEE (acetyltyrosin ethyl ester).

The figure in parentheses shows the percent inhibition at a concentration of the compound of $1 \times 10^{-5}$M.

Inhibition of complement mediated hemolysis (%): The inhibitory activity is shown in terms of percent inhibition of the compound at varied concentrations.

Compound No.: The compound number shown in Examples

TABLE 2

| Compound No. | Anti-C1 activity | | Inhibition of complement mediated hemolysis (%) | | | |
|---|---|---|---|---|---|---|
| | C1r̄ | C1s̄ | 1 × 10$^{-4}$ | 1 × 10$^{-5}$ | 1 × 10$^{-6}$ | 1 × 10$^{-7}$ |
| 1 | | | 99 | 71 | 64 | 10 |
| 2 | | | 99 | 90 | 30 | 8 |
| 3 | 28 | | 98 | 75 | 0 | 0 |
| 4 | 5 × 10$^{-6}$ | | 100 | 99 | 86 | 12 |
| 5 | 2 × 10$^{-6}$ | | 100 | 100 | 81 | 16 |
| 6 | | | 99 | 93 | 14 | 0 |
| 7 | 31 | | 98 | 64 | 13 | 14 |
| 8 | >10$^{-5}$ | | 27 | 15 | 9 | 0 |
| 9 | 28 | | 97 | 72 | 6 | 0 |
| 10 | 46 | | 100 | 99 | 98 | 74 |
| 11 | 5 × 10$^{-6}$ | | 95 | 99 | 82 | 25 |
| 12 | 8 × 10$^{-7}$ | 3 × 10$^{-7}$ | 100 | 100 | 54 | 11 |
| 13 | 21 | | 99 | 31 | 6 | 0 |
| 14 | 38 | | 0 | 74 | 10 | 0 |
| 15 | 10 | | 80 | 10 | 2 | 0 |
| 16 | | | 96 | 34 | 0 | 0 |
| 17 | | | 93 | 97 | 83 | 58 |
| 18 | | | 91 | 38 | 12 | 0 |
| 19 | | | 95 | 98 | 65 | 37 |
| 20 | 1 × 10$^{-6}$ | | 97 | 75 | 38 | 17 |
| 21 | | | 87 | 88 | 37 | 22 |
| 22 | 5 × 10$^{-6}$ | | 88 | 76 | 25 | 11 |
| 23 | | | 98 | 99 | 94 | 42 |
| 24 | | | 76 | 20 | 8 | 0 |
| 25 | | | 62 | 0 | 0 | 0 |
| 26 | 37 | | 38 | 14 | 6 | 0 |
| 27 | | | 100 | 99 | 88 | 44 |
| 28 | 9 × 10$^{-7}$ | | 97 | 71 | 34 | 23 |
| 29 | | | 98 | 93 | 57 | 25 |
| 30 | 1 × 10$^{-6}$ | | 99 | 94 | 62 | 45 |
| 31 | | | 98 | 91 | 65 | 25 |
| 32 | 1 × 10$^{-5}$ | | 73 | 80 | 50 | 32 |
| 33 | | | 92 | 89 | 29 | 7 |
| 34 | | | 100 | 99 | 99 | 86 |
| 35 | 4 × 10$^{-6}$ | 3 × 10$^{-7}$ | 100 | 100 | 97 | 46 |
| 36 | 46 | | 93 | 40 | 8 | 0 |
| 37 | | | 100 | 99 | 95 | 94 |
| 38 | | | 98 | 76 | 27 | 7 |

TABLE 2-continued

| Compound No. | Anti-Cl activity | | Inhibition of complement mediated hemolysis (%) | | | |
|---|---|---|---|---|---|---|
| | $C1\bar{r}$ | $C1\bar{s}$ | $1 \times 10^{-4}$ | $1 \times 10^{-5}$ | $1 \times 10^{-6}$ | $1 \times 10^{-7}$ |
| 39 | $5 \times 10^{-7}$ | | 100 | 99 | 89 | 71 |
| 40 | | | 15 | 3 | 0 | 0 |
| 41 | 20 | | 71 | 10 | 10 | 0 |
| Leupeptin | $2 \times 10^{-4}$ | $2 \times 10^{-5}$ | 97 | 52 | 0 | 0 |

(2) Forssman shock:

The experiment was performed according to the method of I. G. Offerness et al. [Biochem. Pharmacol., 27 (14), 1873–1878 (1978)]. Male Hartlay guinea pig of about 300 g in body weight was used. Each guinea pig of the control group was administered intravenously with 0.5 ml (minimum dose to cause the shock) of hemolysin (commercial hemolysin, 5,000 U as assayed by the method of Ogata) and the time elapsed until death was observed. For the test group, each guinea pig was administered intravenously with the test compound 5 minutes before the administration of hemolysin and the time (second) elapsed until death was observed. The results obtained were as shown in Table 3. As compared with the control group, the administered group showed a significant extension of survival time.

TABLE 3

| | Control group (sec.) | Group administered with compound No. 35 (sec.) | |
|---|---|---|---|
| | | 1 mg/kg | 3 mg/kg |
| 1 | 260 | 490 | 365 |
| 2 | 585 | 375 | Survival |
| 3 | 375 | 255 | 4000 |
| 4 | 225 | 285 | 690 |
| Average | 361 | 351 | 528 |

Method of administration:

The present compound is most suitably administered orally, though can be administered by injection. It is used as a drug either alone or in combination with other drugs. It is administered generally in the form of medicinal composition, though can be administered as simple substance without any additive. Examples of medicinal compositions include tablets, powders, capsules, syrups and solutions. An oral composition may contain common additives such as binders, diluents, lubricants, disintegrators and excipients. Oral solutions may be in the form of aqueous or oily suspension, solution, emulsion, syrup or elixir, or in the form of dry syrup which, before use, is readjusted with water or other suitable solvents. The solutions may contain common additives such as suspending agents, flavoring agents, diluents, or emulsifies. For injection, may be used aqueous suspensions or oily suspensions.

Dosage:

The present compound may be administered to mammals (including man) orally at a dose of 10 to 200 mg per day or by intravenous injection at a dose of 1 to 20 mg per day. However, these doses are presented solely for the sake of example. A suitable dose for a patient should be determined depending upon the age and body weight of the patient and the features of illness.

Examples of pharmaceutical formulations are described below.

Examples of pharmaceutical formulations:

| (1) | Capsules | | |
|---|---|---|---|
| | The present compound | 100.0 | mg |
| | Lactose | 59.0 | |
| | Crystalline cellulose | 33.4 | |
| | Calcium carboxymethylcellulose | 3.6 | |
| | Magnesium stearate | 4.0 | |
| | Total | 200.0 | mg |
| (2) | Fine granules | | |
| | The present compound | 50.0 | mg |
| | Lactose | 249.0 | |
| | Mannitol | 75.0 | |
| | Corn starch | 110.0 | |
| | Hydroxypropylcellulose | 16.0 | |
| | Total | 500.0 | mg |
| (3) | Injections | | |
| | The present compound | 5.0 | mg |
| | Water for injection | 2 | ml |

Make up to injections in a customary manner.

Toxicity:

The median lethal does ($LD_{50}$) of the present compound is as shown in Table 4.

TABLE 4

| Compound No. | $LD_{50}$ mg/kg | |
|---|---|---|
| | IP | PO |
| 35 | 133 | 1,200 |
| 34 | 200 | 2,500 |

Examples of preparation of the present compounds are described below. The physical data of each compound are summarized in Table 5. Synthesis of acetylcoumaric acid:

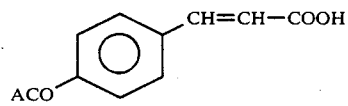

Into a 3-liter pear-shaped flask, were charged 500 g (4.1 moles) of p-hydroxybenzaldehyde, 1.5 kg (3 equivalents) of acetic anhydride, and 773 g (2.3 equivalents) of sodium acetate. After having been attached with an air condenser, the flask was heated for 20 hours in an oil bath at 145° C. During the reaction, the flask was stirred at times to disintegrate the solid components. The hot reaction mixture, which had turned into a red solution, was poured into 40 liters of hot water and stirred. The precipitated ocher-yellow crystals were collected by filtration, dried, and stirred in 5 liters of hot methanol. The supernatant was concentrated to evaporate the methanol and the precipitated crystals were collected by filtration and dried. Yield, 430 g (51%); melting point, 168°–172° C.; IR, $\nu_{max.}^{KBr}$, cm$^{-1}$: 3000–2500, 1740. Synthesis of acetylcoumaryl chloride:

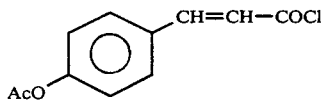

To a suspension of 180 g of acetylcoumaric acid in 1.5 l of ethyl acetate, was added with stirring 240 g of phosphorus pentachloride. With the progress of reaction, the reactant mixture turned into a brown clear solution. After having been left standing overnight, the reaction mixture was concentrated under reduced pressure. The precipitated crystals were collected by filtration and washed with hexane to obtain pale yellow crystals. Yield, 180 g (92%). Synthesis of acetylcoumaramide:

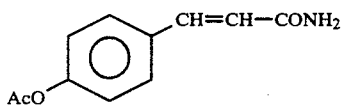

In 1.5 liters of ethyl acetate, was suspended 200 g of acetylcoumaryl chloride. A sufficient quantity of vaporized ammonia was fed to the suspension while stirring at room temperature. The suspension changed in appearance, becoming whitish in color. After having been left standing overnight, the suspension was filtered. The collected crystals were thoroughly washed successively with ethyl acetate, saturated aqueous sodium bicarbonate solution, and water, and air-dried. Yield, 76.9 g (44%); melting point, 150°–153° C. IR, $\nu_{max}^{KBr}$, cm$^{-1}$: 3300, 3150, 1755, 1660. Synthesis of 4-($\beta$-amidinoethenyl)phenol methanesulfonate:

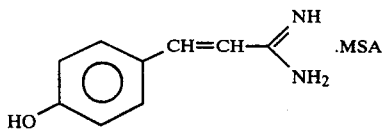

In 1.5 liters of anhydrous methylene chloride, was suspended 173 g (0.82 mole) of coumaramide. To the suspension, while being stirred at room temperature, was added dropwise a solution of 204 g (1.3 equivalents) of Meerwein reagent [(C$_2$H$_5$)$_3$O$^+$BF$_4^-$] in 1.0 liter of anhydrous methylene chloride. The reacting mixture gradually turned into a clear solution. After having been left standing overnight, the brown solution was concentrated to about 300 ml. After addition of 1.5 liters of anhydrous methanol, vaporized ammonia was blown into the stirred solution for 3 hours at room temperature (exothermic reaction). The reaction mixture was left standing overnight and the resulting brown solution was freed from the insolubles by filtration. Water was added to the filtrate to precipitate yellow crystals which were collected by filtration, washed with acetone, and air-dried. The yield of the free base was 121 g (91%).

The above free base was suspended in 150 ml of methanol, and to the suspension was added with stirring at room temperature 85 g (1.2 equivalents) of methanesulfonic acid. Ethyl ether was added to the resulting clear solution to precipitate crystals which were collected by filtration and air-dried. Yield, 127 g (67%); melting point, 147°–149° C. IR, $\nu_{max}^{KBr}$, cm$^{-1}$: 3350, 3100 (NH, OH), 1670 (C=N).

Example 1 Synthesis of 4-($\beta$-amidinoethenyl)phenyl acetate:

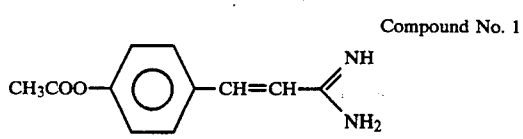

Compound No. 1

To a mixture of 8 ml of glacial acetic acid and 8 ml of acetyl chloride, was added 2.0 g of 4-($\beta$-amidinoethenyl)phenol methanesulfonate. The mixture was heated with stirring under reflux for one hour. After cooling, the reaction mixture was mixed with ethyl ether to precipitate a white solid substance which was recrystallized from ethanol to yield 1.8 g of colorless needle crystals of 4-($\beta$-amidinoethenyl)phenyl acetate methanesulfonate.

Example 2 Synthesis of 4-($\beta$-amidinoethenyl)phenyl isovalerate:

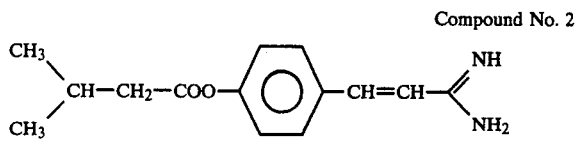

Compound No. 2

Into 10 ml of dried pyridine, was dissolved 1.0 g of isovaleric acid. To the solution, while being cooled in ice, was added 2.5 g of DCC. After 30 minutes of stirring, 2.6 g of 4-($\beta$-amidinoethenyl)phenol methanesulfonate was added and the mixture was stirred overnight at room temperature. The reaction mixture was removed of precipitated DCU by filtration and the DCU was washed with pyridine. Ethyl ether was added to the combined filtrate to precipitate a white solid substance which was collected by filtration, washed with ethyl ether, and recrystallized from ethanol to yield 1.7 g of colorless flaky crystals of 4-($\beta$-amidinoethenyl)phenyl isovalerate methanesulfonate.

Example 3 Synthesis of 4-($\beta$-amidinoethenyl)phenyl cyclopropanecarboxylate:

Compound No. 5

To a solution of 2.1 g of 4-($\beta$-amidinoethenyl)phenol methanesulfonate in 20 ml of dried pyridine, while being cooled in ice and stirred, was added slowly 0.8 g of cyclopropanecarbonyl chloride. The mixture was then stirred at room temperature for 30 minutes. The reaction mixture was removed of precipitated white crystals by filtration and the crystals were washed with pyridine. Ethyl ether was added to the combined filtrate to precipitate an oily substance. The oily substance was separated from the supernatant, washed a few times with ethyl ether, and dissolved in water. To the resulting aqueous solution, was added with stirring a saturated aqueous sodium bicarbonate solution to precipitate a yellow solid substance. The precipitate was collected by filtration and washed with water, then with acetone to obtain 1.9 g of carbonate of the captioned compound. The carbonate was suspended in 10 ml of methanol and admixed with 0.8 g of methanesulfonic acid followed by ethyl ether to obtain a white substance which upon recrystallization from ethanol yielded 1.6 g of colorless flaky crystals of 4-(β-amidinoethenyl)-phenyl cyclopropanecarboxylate methanesulfonate.

Example 4 Synthesis of 4-(β-amidinoethenyl)phenyl 6-benzyloxycarbonylaminocaproate.

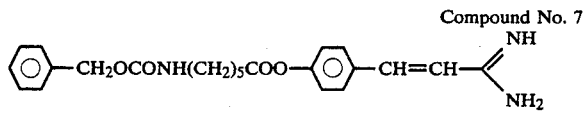

Compound No. 7

To a solution of 4.5 g of 6-benzyloxycarbonylaminocaproic acid in 45 ml of dried pyridine, while being cooled in ice, was added 4.2 g of DCC. After 30 minutes of stirring, 4.4 g of 4-(β-amidinoethenyl)phenol methanesulfonate was added to the solution and stirred overnight at room temperature. The reaction mixture was freed from the precipitated DCU by filtration and the DCU was washed with pyridine. Ethyl ether was added to the combined filtrate to precipitate an oily substance. The oily substance was separated from the supernatant, washed a few times with ethyl ether, and dissolved in ethanol. Ethyl ether was added to the ethanol solution to precipitate a white solid substance which on recrystallization from an ethanol-ethyl ether mixture yielded 4.8 g of colorless granular crystals of 4-(β-amidinoethenyl)phenyl 6-benzyloxycarbonylaminocaproate methanesulfonate.

Example 5 Synthesis of 4-(β-amidinoethenyl)phenyl 6-aminohexanoate:

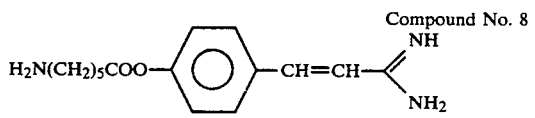

Compound No. 8

To 9 ml of 30% hydrogen bromide-acetic acid mixture, was added 2.5 g of 4-(5-amidinoethenyl)phenyl 6-benzyloxycarbonylaminohexanoate methanesulfonate. The mixture was stirred at room temperature, during which the crystals once dissolved, forming a yellow clear solution, but after a short period of stirring there appeared new crystals. Upon addition of anhydrous ethyl ether to the reaction mixture, a viscous substance containing crystals precipitated. The supernatant was removed and the residue was washed several times with ethyl ether. Upon twice recrystallization from an ethanolethyl ether mixture, there were obtained 1.3 g of white crystals of 4-(β-amidinoethenyl)phenyl 6-aminohexanoate dihydrobromide.

Example 6 Synthesis of 4-(β-amidinoethenyl)phenyl 6-guanidinocaproate:

minutes of stirring, 2.6 g of 4-(β-amidinoethenyl)phenol methanesulfonate was added and the mixture was stirred overnight. The insolubles were separated by filtration, suspended in DMF, and removed by filtration. Ethyl ether was added to the combined filtrate to precipitate an oily substance. The oily substance was separated, added to a saturated aqueous sodium bicarbonate solution and stirred to precipitate yellow crystals. The crystals were suspended in ethanol and admixed with methanesulfonic acid to form a clear solution. Ethyl ether was added to the solution and the precipitated crystals were collected by filtration and recrystallized from ethanol to obtain 1.8 g of 4-(β-amidinoethenyl)phenyl 6-guanidinocaproate dimethanesulfonate.

Example 7 Synthesis of 4-(β-amidinoethenyl)phenyl trans-4-aminomethylcyclohexanecarboxylate:

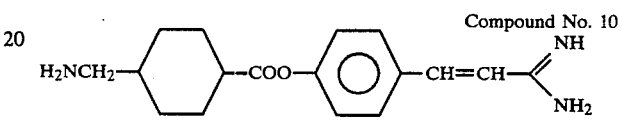

Compound No. 10

To a mixture of 9 ml of a 30% hydrogen bromideacetic acid mixture and 18 ml of glacial acetic acid, was added 2.7 g of 4-(β-amidinoethenyl)phenyl trans-4-benzyloxycarbonylaminomethylcyclohexanecarboxylate methanesulfonate. After stirring the mixture for one hour at room temperature, anhydrous ethyl ether was added to wash out a white solid substance. The solid substance was recrystallized from ethanol to obtain 1.1 g of a white powder of 4-(β-amidinoethenyl)phenyl trans-4-aminomethylcyclohexane carboxylate dihydrobromide.

Example 8 Synthesis of 4-(β-amidinoethenyl)phenyl trans-4-benzyloxycarbonylaminomethylcyclohexanecarboxylate:

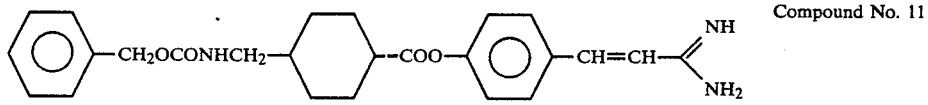

Compound No. 11

To a solution of 5.0 g of trans-4-benzyloxycarbonylaminomethylcyclohexanecarboxylic acid in 50 ml of dried pyridine, while being cooled in ice, was added 4.2 g of DCC. After 30 minutes of stirring, to the mixture was added 4.4 g of 4-(β-amidinoethenyl)phenol methanesulfonate. The mixture was stirred overnight at room temperature. The DCU precipitated from the reaction mixture was separated by filtration and washed with pyridine. Ethyl ether was added to the combined filtrate to precipitate a white substance which was collected by filtration, washed with ethyl ether, and recrystallized from ethanol to yield 5.7 g of colorless needle crystals of 4-(β-amidinoethenyl)pnenyl trans-4-benzyloxycarbonylaminomethylcyclohexanecarboxylate methanesulfonate.

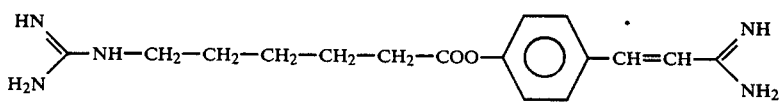

Compound No. 9

To a solution of 2.1 g of 6-quanidinocaproic acid in 50 ml of dried pyridine, was added 3.1 g of DCC. After 30

Example 9 Synthesis of 4-(β-amidinoethenyl)-phenyl benzoate:

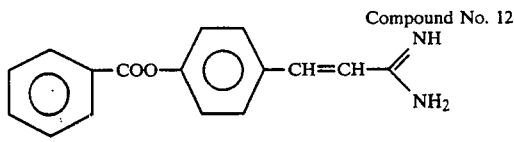
Compound No. 12

To a solution of 500 mg of 4-(β-amidinoethenyl)-phenol methanesulfonate in 5 ml of pyridine, while being cooled in ice, was added 300 mg of benzoyl chloride. The resulting solution was stirred overnight at room temperature, then admixed with ethyl ether, again stirred thoroughly, and the ether layer was removed by decantation. This treatment was repeated once more and the residual solid substance was recrystallized from a methanol-ethyl ether mixture to obtain 4-(β-amidinoethenyl)-phenyl benzoate methanesulfonate.

Example 10 Synthesis of 4-(β-amidinoethenyl)phenyl phenylacetate:

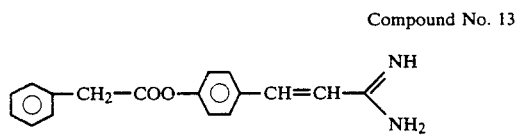
Compound No. 13

To a solution of 1.4 g of phenylacetic acid in 50 ml of dried pyridine, was added 3.1 g of DCC. After 30 minutes of stirring, 2.6 g of 4-(β-amidinoethenyl)phenol methanesulfonate was added to the mixture and stirred overnight. The insolubles were removed by filtration and ethyl ether was added to the filtrate to precipitate crystals. The crystals were collected by filtration and recrystallized from ethanol to obtain 1.5 g of 4-(β-amidinoethenyl)phenyl phenylacetate methanesulfonate.

Example 11 Synthesis of 4-(β-amidinoethenyl)phenyl 4-phenylbutyrate:

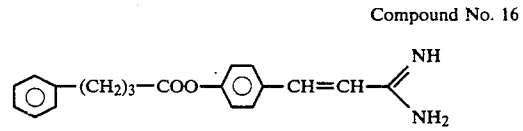
Compound No. 16

To a solution of 1.6 g of 4-phenylbutyric acid in 50 ml of dried pyridine, was added 3.1 g of DCC. After 30 minutes of stirring, 2.6 g of 4-(β-amidinoethenyl)-phenol methanesulfonate was added and the mixture was stirred overnight. The insolubles were removed by filtration and ethyl ether was added to the filtrate to precipitate crystals. The crystals were collected by filtration and recrystallized from ethanol to obtain 2.2 g of 4-(β-amidinoethenyl)phenyl 4-phenylbutyrate methanesulfonate.

Example 12 Synthesis of 4-(β-amidinoethenyl)phenyl cinnamate:

Compound No. 17

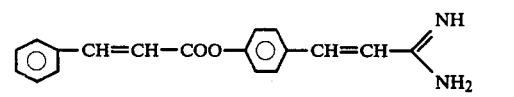

To a mixture of 1.5 g of cinnamic acid and 2.5 g of DCC, was added 20 ml of dried pyridine. After 30 minutes of stirring, to the mixture was added 2.6 g of 4-(β-amidinoethenyl)phenol methanesulfonate. The mixture was stirred overnight. The precipitate was collected by filtration, washed with pyridine, and then with ethyl ether. The washed precipitate was added to 50 ml of DMF. The insolubles were removed by filtration and ethyl ether was added to the filtrate to precipitate a white solid substance which was recrystallized from ethanol to obtain 1.4 g of colorless needle crystals. On the other hand, pale yellow crystals were formed by the addition of ethyl ether to the pyridine solution obtained above as the filtrate. Upon recrystallization from ethanol, these crystals gave 0.8 g of colorless needle crystals of 4-(β-amidinoethenyl)phenyl cinnamate methanesulfonate. The total yield, therefore, was 2.2 g.

Example 13 Synthesis of 4-(β-amidinoethenyl)phenyl 4-guanidinobenzoate:

Compound No. 35

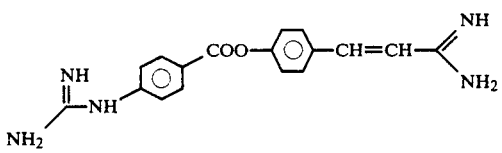

To a solution of 106 g of 4-guanidinobenzoic acid hydrochloride in 1.3 liters of pyridine, while being cooled in ice and stirred; was added 122 g of DCC. After 30 minutes of stirring, to the mixture was added slowly 127 g of 4-(β-amidinoethenyl)phenol methanesulfonate. The resulting clear solution was stirred overnight and the precipitated solid substance was collected by filtration. The solid substance was suspended in 2 liters of water, thoroughly stirred, and filtered. To the filtrate was added at room temperature about 2 liters of saturated aqueous sodium bicarbonate solution. The mixture was stirred and the precipitated crystals were collected by filtration, washed with water, and then with acetone. After air-drying for a short time, the orange-yellow crystals were suspended in 200 ml of methanol and admixed with about 100 g (2 equivalents) of methanesulfonic acid while stirring at room temperature. Ethyl ether was added to the reaction mixture to precipitate crystals which were collected by filtration. The crystals were suspended in methanol and converted again to the carbonate. The carbonate was suspended in 300 ml of ethanol at room temperature and admixed with methanesulfonic acid to turn the suspension into a clear solution. The solution was stirred for a while to precipitate crystals which were collected by filtration at room temperature and thoroughly washed with cold ethanol. The yield was 45 g (18%).

Example 14

The following compounds were obtained by the procedures similar to those of Examples 1 to 13:

| Compound No. | $R_1$ |
|---|---|
| 1 | $CH_3-$ |

-continued $$R_1-COO-\underset{}{\underset{}{\bigcirc}}-CH=CH-\underset{NH_2}{\overset{NH}{\underset{\|}{C}}}$$

| Compound No. | R₁ |
|---|---|
| 2 | (CH₃)₂CH—CH₂— |
| 3 | n-C₆H₁₃— |
| 4 | CH₃—CH=CH—CH=CH— |
| 5 | cyclopropyl |
| 6 | cyclopentyl; cyclohexyl; cyclopentenyl; C₆H₅—CH₂OCONH—CH₂—; H₂N—CH₂— |
| 7 | C₆H₅—CH₂O—CONH—(CH₂)₅— |
| 8 | H₂N—(CH₂)₅—; H₂N(HN=)C—NH—CH₂— (with H₂N) |
| 9 | H₂N(HN=)C—NH—(CH₂)₅— |
| 10 | H₂NCH₂—C₆H₄— |
| 11 | C₆H₅—CH₂OCONHCH₂—C₆H₁₀—; H₂N(HN=)C—NH—CH₂—C₆H₁₀— |
| 12 | C₆H₅— |
| 13 | C₆H₅—CH₂— |
| 14 | (CH₃)₂CH—CH₂—C₆H₄—CH(CH₃)₂ |
| 15 | C₆H₅—CH₂CH₂— |
| 15 | C₆H₅—CH(CH₃)— |
| 16 | C₆H₅—CH₂CH₂CH₂— |
| 17 | C₆H₅—CH=CH— |
| | C₆H₅—CH=C(CH₃)— |
| | C₆H₅—CH=C(C₂H₅)— |
| 18 | o-CH₃—C₆H₄— |
| 19 | m-CH₃—C₆H₄— |
| 20 | p-CH₃—C₆H₄— |
| 21 | 3,4-(CH₃)₂—C₆H₃— |
| 22 | p-tC₄H₉—C₆H₄— |
| | p-CH₃—C₆H₄—CH=CH— |
| 23 | p-CH₃O—C₆H₄— |
| 24 | 3,4-(CH₃O)₂—C₆H₃— |
| | p-n-C₄H₉—O—C₆H₄— |

-continued $R_1-COO-\underset{}{\bigcirc}-CH=CH-\underset{NH_2}{\overset{NH}{C}}$

| Compound No. | $R_1$ |
|---|---|
| 25 | 4-CH3O-C6H4-CH2- |
| | 4-CH3O-C6H4-CH2CH2- |
| | 4-CH3O-C6H4-CH=CH- |
| 26 | C6H5-CH2O-C6H4- |
| | 4-HO-C6H4- |
| 27 | 3,4-methylenedioxyphenyl- |
| | 3,4-methylenedioxyphenyl-CH2CH2- |
| | 3,4-methylenedioxyphenyl-CH=CH- |
| 28 | 4-CH3S-C6H4- |
| 29 | 4-CH3OOC-C6H4- |
| | 4-tC4H9OOC-C6H4- |
| | 4-HOOC-C6H4- |
| 30 | 4-OHC-C6H4- |
| | 4-CH3O-C6H4- |
| | 4-CH3COO-C6H4- |

-continued $R_1-COO-\underset{}{\bigcirc}-CH=CH-\underset{NH_2}{\overset{NH}{C}}$

| Compound No. | $R_1$ |
|---|---|
| | 4-(CH3OOC)-C6H4-CH=CH- |
| 31 | 4-CH3CONH-C6H4- |
| | 4-H2N-C6H4- |
| 32 | 4-(CH3)2N-C6H4- |
| | 3,N,N-trimethylaminophenyl- |
| 33 | 4-(C6H5CH2OCONHCH2)-C6H4- |
| 34 | 4-H2NCH2-C6H4- |
| | 4-(C6H5CH2OCONHCH2CH2)-C6H4- |
| | 4-H2NCH2CH2-C6H4- |
| 35 | 4-(H2N-C(=NH)-NH)-C6H4- |
| | 4-(CH3NH-C(=NH)-NH)-C6H4- |
| | 4-(H2N-C(=NH)-N(CH3))-C6H4- |

-continued
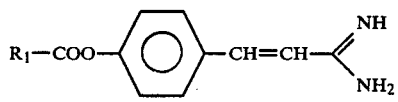
| Compound No. | $R_1$ |
|---|---|
| 36 | 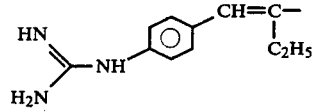 |
| 37 | 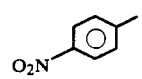 |
| 38 | 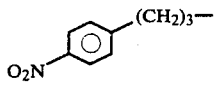 |
| | 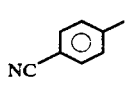 |
| | 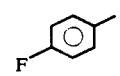 |
-continued
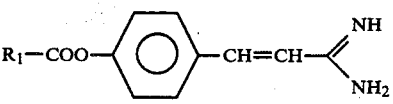
| Compound No. | $R_1$ |
|---|---|
| 39 | 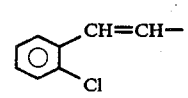 |
| 40 |  |
| | 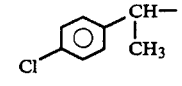 |
| 41 | 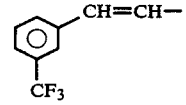 |
TABLE 5
| Compound No. | Salt | Mp °C. | IR $\nu_{max}^{KBr}$ cm$^{-1}$ | | NMR(DMSO-d$_6$) δ:(J;Hz) |
|---|---|---|---|---|---|
| 1 | MSA | 198–199 | 3300 | 3100 | 2.28(3H,s) |
| | | | 1770 | 1685 | 2.52(3H,s) |
| | | | 1645 | 1510 | 6.82(1H,d,J = 16.0) |
| | | | 1190 | 1165 | 7.27(2H,d,J = 8.5) |
| | | | | | 7.73(2H,d,J = 8.5) |
| | | | | | 7.92(1H,d,J = 16.0) |
| | | | | | 8.83(2H,br) |
| | | | | | 9.13(2H,br) |
| 2 | MSA | 206–207 | 3270 | 3100 | 1.01(6H,d,J = 6.0) |
| | | | 2950 | 1760 | 1.35–2.30(1H,m) |
| | | | 1685 | 1645 | 2.48(2H,d,J = 6.0) |
| | | | 1600 | 1510 | 2.53(3H,s) |
| | | | 1210 | 1170 | 6.82(1H,d,J = 16.0) |
| | | | | | 7.20(2H,d,J = 8.5) |
| | | | | | 7.70(2H,d,J = 8.5) |
| | | | | | 7.90(1H,d,J = 16.0) |
| | | | | | 8.82(2H,br) |
| | | | | | 9.10(2H,br) |
| 3 | MSA | 140–142 | 3250 | 3050 | 0.70–2.00(13H,m) |
| | | | 1750 | 1680 | 2.47(3H,s) |
| | | | 1640 | 1180 | 6.80(1H,d,J = 16.0) |
| | | | | | 7.90(1H,d,J = 16.0) |
| | | | | | 7.25(2H,d,J = 9.2) |
| | | | | | 7.69(2H,d,J = 9.2) |
| | | | | | 8.80(2H,br) |
| | | | | | 9.10(2H,br) |
| 4 | MSA | 195–196 | 3280 | 3050 | 1.87(3H,d,J = 3.6) |
| | | | 1722 | 1680 | 2.47(3H,s) |
| | | | 1635 | 1190 | 5.87–8.13(10H,m) |
| | | | | | 8.82(2H,br) |
| | | | | | 9.10(2H,br) |
| 5 | MSA | 197–199 | 3270 | 3100 | 1.06(4H,d,J = 7.0) |
| | | | 1740 | 1690 | 1.63–2.13(1H,m) |
| | | | 1645 | 1510 | 2.50(3H,s) |
| | | | 1185 | 1205 | 6.77(1H,d,J = 16.0) |
| | | | | | 7.20(2H,d,J = 8.5) |
| | | | | | 7.67(2H,d,J = 8.5) |
| | | | | | 7.83(1H,d,J = 16.0) |
| | | | | | 8.77(2H,br) |
| | | | | | 9.04(2H,br) |
| 6 | MSA | 218–220 | 3250 | 3100 | 1.00–2.20(11H,br) |
| | | | 1755 | 1680 | 2.43(3H,s) |
| | | | 1200 | | 6.73(1H,d,J = 17.0) |

TABLE 5-continued

| Compound No. | Salt | Mp °C. | IR$\nu_{max}^{KBr}$ | cm$^{-1}$ | NMR(DMSO-d$_6$) δ:(J;Hz) |
|---|---|---|---|---|---|
| | | | | | 7.83(1H,d,J = 17.0) |
| | | | | | 7.19(2H,d,J = 9.0) |
| | | | | | 7.66(2H,d,J = 9.0) |
| | | | | | 8.73(2H,br) |
| | | | | | 9.03(2H,br) |
| 7 | MSA | 113.5–115.5 | 3320 | 3100 | 1.17–1.97(6H,br) |
| | | | 2930 | 1755 | 2.27–3.23(4H,br) |
| | | | 1690 | 1510 | 2.45(3H,s) |
| | | | 1220 | 1205 | 4.98(2H,s) |
| | | | | | 6.72(1H,d,J = 16.0) |
| | | | | | 7.00–8.03(11H,m) |
| | | | | | 8.72(2H,br) |
| | | | | | 9.00(2H,br) |
| 8 | 2HBr | | 3300 | 3050 | |
| | | | 1755 | 1670 | |
| | | | 1640 | 1505 | |
| | | | 1165 | | |
| 9 | 2MSA | 142–143 | 3250 | 3100 | 1.13–2.00(8H,br) |
| | | | 1752 | 1640 | 2.50(3H,s) |
| | | | 1180 | | 3.35(2H,br) |
| | | | | | 6.62–8.17(10H,m) |
| | | | | | 8.80(2H,br) |
| | | | | | 9.10(2H,br) |
| 10 | 2HBr | 203–205 | 3270 | 3080 | 0.70–2.93(12H,br) |
| | | | 1750 | 1673 | 6.83(1H,d,J = 16.0) |
| | | | 1640 | 1510 | 7.22(2H,d,J = 8.5) |
| | | | 1165 | | 7.53–8.20(6H,m) |
| | | | | | 8.67(2H,br) |
| | | | | | 9.15(2H,br) |
| 11 | MSA | 166–169 | 3350 | 3100 | 0.67–2.60(10H,br) |
| | | | 2920 | 1745 | 2.47(3H,s) |
| | | | 1690 | 1510 | 2.73–3.10(2H,br) |
| | | | 1235 | 1220 | 5.03(2H,s) |
| | | | | | 6.77(1H,d,J = 16.0) |
| | | | | | 7.07–8.07(11H,m) |
| | | | | | 8.77(2H,br) |
| | | | | | 9.06(2H,br) |
| 12 | MSA | 185–193 | 3400 | 3050 | |
| | | | 1730 | 1210 | |
| 13 | MSA | 163–164 | 3350 | 3140 | 2.48(3H,s) |
| | | | 1765 | 1685 | 3.98(2H,s) |
| | | | 1205 | | 6.79(1H,d,J = 17.0) |
| | | | | | 7.07–8.10(10H,m) |
| | | | | | 8.83(2H,br) |
| | | | | | 9.13(2H,br) |
| 14 | MSA | 118–119 | 3300 | 3120 | |
| | | | 1750 | 1675 | |
| | | | 1188 | | |
| 15 | MSA | 178–180 | 3300 | 3100 | 2.47(3H,s) |
| | | | 1750 | 1690 | 2.95(4H,br) |
| | | | 1652 | 1510 | 6.53–8.07(11H,m) |
| | | | 1240 | 1200 | 8.78(2H,br) |
| | | | 1150 | | 9.08(2H,br) |
| 16 | MSA | 150–151 | 3250 | 3100 | 1.73–2.30(2H,m) |
| | | | 1760 | 1688 | 2.52(3H,s) |
| | | | 1250 | 1165 | 2.43–3.13(4H,m) |
| | | | | | 6.77(1H,d,J = 16.0) |
| | | | | | 6.68–8.07(10H,m) |
| | | | | | 8.75(2H,br) |
| | | | | | 9.07(2H,br) |
| 17 | MSA | 203–206 | 3300 | 3100 | 2.53(3H,s) |
| | | | 1735 | 1675 | 6.60–8.20(13H,m) |
| | | | 1635 | 1510 | 8.83(2H,br) |
| | | | 1210 | | 9.14(2H,br) |
| 18 | MSA | 151–152 | 3280 | 3100 | 2.43(3H,s) |
| | | | 1735 | 1680 | 2.58(3H,s) |
| | | | 1640 | 1210 | 6.80(1H,d,J = 16.0) |
| | | | | | 7.23–8.27(9H,m) |
| | | | | | 8.78(2H,br) |
| | | | | | 9.08(2H,br) |
| 19 | MSA | 141–142 | 3320 | 3110 | 2.43(3H,s) |
| | | | 1735 | 1680 | 2.45(3H,s) |
| | | | 1160 | | 6.82(1H,d,J = 17.0) |
| | | | | | 7.25–8.22(9H,m) |
| | | | | | 8.83(2H,br) |
| | | | | | 9.15(2H,br) |
| 20 | MSA | 222–223 | 3300 | 3100 | 2.40(3H,s) |
| | | | 1730 | 1685 | 2.47(3H,s) |
| | | | 1165 | | 6.78(1H,d,J = 16.2) |

TABLE 5-continued

| Compound No. | Salt | Mp °C. | IR$\nu_{max}^{KBr}$ | cm$^{-1}$ | NMR(DMSO-d$_6$) δ:(J;Hz) |
|---|---|---|---|---|---|
| | | | | | 4.32–4.90(9H,m) |
| | | | | | 8.80(2H,br) |
| | | | | | 9.10(2H,br) |
| 21 | MSA | 201–204.5 | 3200 | 3120 | 2.30(6H,br) |
| | | | 1733 | 1690 | 2.53(3H,s) |
| | | | 1645 | 1510 | 6.83(1H,d,J = 16.0) |
| | | | 1292 | 1257 | 7.17–8.17(9H,m) |
| | | | 1215 | 1195 | 8.85(2H,br) |
| | | | | | 9.13(2H,br) |
| 22 | MSA | 255–260 | 3300 | 3120 | 1.33(9H,s) |
| | | | 2960 | 1735 | 2.53(3H,s) |
| | | | 1680 | 1645 | 6.88(1H,d,J = 16.0) |
| | | | 1600 | 1510 | 7.37–8.30(9H,m) |
| | | | 1260 | 1190 | 8.98(2H,br) |
| | | | | | 9.20(2H,br) |
| 23 | MSA | 223–224 | 3340 | 3120 | 2.55(3H,s) |
| | | | 1733 | 1690 | 3.85(3H,s) |
| | | | 1605 | 1515 | 6.65–8.28(10H,m) |
| | | | 1255 | 1200 | 8.87(2H,br) |
| | | | | | 9.15(2H,br) |
| 24 | MSA | 150–153 | 3320 | 3120 | 2.53(3H,s) |
| | | | 1735 | 1680 | 3.85(3H,s) |
| | | | 1645 | 1600 | 3.87(3H,s) |
| | | | 1510 | 1270 | 6.63–8.17(9H,m) |
| | | | 1210 | 1170 | 8.83(2H,br) |
| | | | | | 9.13(2H,br) |
| 25 | MSA | 165–168 | 3450 | 2850 | 2.48(3H,s) |
| | | | 1765 | 1675 | 2.88(4H,br) |
| | | | 1640 | 1510 | 3.70(3H,s) |
| | | | 1190 | | 6.52–8.02(10H,m) |
| | | | | | 8.77(2H,br) |
| | | | | | 9.07(2H,br) |
| 26 | MSA | 216–219 | 3350 | 3170 | 2.47(3H,s) |
| | | | 1730 | 1680 | 5.30(2H,s) |
| | | | 1645 | 1610 | 6.75–8.48(15H,m) |
| | | | 1515 | 1280 | 8.69(2H,br) |
| | | | 1220 | 1200 | 8.99(2H,br) |
| 27 | MSA | 194–195 | 3700–2900 | | |
| | | | 1725 | 1670 | 2.50(3H,s) |
| | | | 1642 | 1445 | 6.18(2H,s) |
| | | | 1280 | 1220 | 6.59–8.13(9H,m) |
| | | | 1165 | | 8.79(2H,br) |
| | | | | | 9.09(2H,br) |
| 28 | MSA | 205–207 | 3330 | 3100 | 2.42(3H,s) |
| | | | 1722 | 1685 | 2.55(3H,s) |
| | | | 1180 | | 6.77(1H,d,J = 16.0) |
| | | | | | 7.17–8.20(9H,m) |
| | | | | | 8.75(2H,br) |
| | | | | | 9.08(2H,br) |
| 29 | MSA | 218.5–220 | 3300 | 3120 | 2.57(3H,s) |
| | | | 1735 | 1725 | 3.90(3H,s) |
| | | | 1675 | 1510 | 6.85(1H,d,J = 16.0) |
| | | | 1265 | 1190 | 7.23–8.40(9H,m) |
| | | | | | 8.83(2H,br) |
| | | | | | 9.10(2H,br) |
| 30 | MSA | 217(dec.) | 3300 | 3100 | 2.55(3H,s) |
| | | | 1735 | 1700 | 6.88(1H,d,J = 17.0) |
| | | | 1675 | 1190 | 7.97(1H,d,J = 17.0) |
| | | | | | 7.48(2H,d,J = 7.2) |
| | | | | | 7.83(2H,d,J = 7.2) |
| | | | | | 8.13(2H,d,J = 7.4) |
| | | | | | 8.38(2H,d,J = 7.4) |
| | | | | | 8.88(2H,br) |
| | | | | | 9.18(2H,br) |
| | | | | | 10.18(1H,s) |
| 31 | MSA | >250 | 3250 | 3100 | (in TFA) |
| | | | 1730 | 1675 | 2.53(3H,s) |
| | | | 1600 | 1530 | 3.13(3H,s) |
| | | | 1260 | 1205 | 6.72(1H,d,J = 16.0) |
| | | | 1160 | | 7.17–8.50(14H,m) |
| | | | | | 9.48(1H,br) |
| 32 | MSA | 212–214 | 3300 | 3100 | 2.52(3H,s) |
| | | | 1710 | 1685 | 3.02(6H,s) |
| | | | 1610 | 1280 | 6.58–8.18(10H,m) |
| | | | 1230 | 1180 | 8.85(2H,br) |
| | | | | | 9.15(2H,br) |
| 33 | MSA | 168–171 | 3300 | 3110 | 2.48(3H,S) |
| | | | 1735 | 1685 | 4.33(2H,d,J = 6.0) |
| | | | 1510 | 1265 | 5.05(2H,s) |

TABLE 5-continued

| Compound No. | Salt | Mp °C. | IR$\nu_{max}^{KBr}$ cm$^{-1}$ | | NMR(DMSO-d$_6$) δ:(J;Hz) |
|---|---|---|---|---|---|
| | | | 1228 | 1210 | 6.78(1H,d,J = 16.0) |
| | | | | | 7.22–8.22(16H,m) |
| | | | | | 8.76(2H,br) |
| | | | | | 9.08(2H,br) |
| 34 | 2HBr | >240 | 3325 | 3100 | 4.00–4.40(2H,br) |
| | | | 1740 | 1672 | 6.87(1H,d,J = 16.0) |
| | | | 1640 | 1267 | 7.27–8.30(10H,m) |
| | | | | | 8.30–8.90(5H,br) |
| | | | | | 9.16(2H,br) |
| 35 | 2MSA | 94–97 | 3400 | 3050 | 2.50(3H,s) |
| | | | 1730 | 1195 | 6.67–8.42(13H,m) |
| | | | | | 8.67–9.30(4H,br) |
| | | | | | 10.33(1H,br) |
| 36 | 2MSA | 126–131 | 3300 | 3140 | 1.25(3H,br) |
| | | | 1720 | 1675 | 2.50(6H,s) |
| | | | 1190 | 1050 | 2.50–2.93(2H,br) |
| | | | | | 6.80(1H,d,J = 16.0) |
| | | | | | 7.17–8.13(14H,m) |
| | | | | | 8.80(2H,br) |
| | | | | | 9.10(2H,br) |
| | | | | | 10.02(1H,br) |
| 37 | MSA | 255–258 (dec.) | 3300 | 3100 | 2.48(3H,s) |
| | | | 1742 | 1685 | 6.87(1H,d,J = 16.0) |
| | | | 1200 | | 7.97(1H,d,J = 16.0) |
| | | | | | 7.52(2H,d,J = 9.0) |
| | | | | | 7.85(2H,d,J = 9.0) |
| | | | | | 8.43(4H,s) |
| | | | | | 8.87(2H,br) |
| | | | | | 9.17(2H,br) |
| 38 | MSA | 140–142 | 3250 | 3080 | 1.80–2.33(2H,m) |
| | | | 1752 | 1690 | 2.47(3H,s) |
| | | | 1512 | 1345 | 2.40–3.07(4H,m) |
| | | | 1165 | | 6.53–8.33(10H,m) |
| | | | | | 8.75(2H,br) |
| | | | | | 9.07(2H,br) |
| 39 | MSA | 236–239 | 3320 | 3100 | 2.55(3H,s) |
| | | | 1738 | 1685 | 6.88(1H,d,J = 16.0) |
| | | | 1640 | 1590 | 7.28–8.31(9H,m) |
| | | | 1510 | 1260 | 8.85(2H,br) |
| | | | 1200 | | 9.15(2H,br) |
| 40 | MSA | 178–182 | 3350 | 3100 | 2.50(3H,s) |
| | | | 1720 | 1675 | 6.57–8.33(12H,m) |
| | | | 1600 | 1510 | 8.82(2H,br) |
| | | | 1220 | ·1190 | 9.12(2H,br) |
| 41 | MSA | 160–164 | 3300 | 3100 | 2.48(3H,s) |
| | | | 1730 | 1680 | 6.60–8.27(12H,m) |
| | | | 1640 | 1510 | 8.82(2H,br) |
| | | | 1330 | 1190 | 9.12(2H,br) |
| | | | 1165 | | |

What is claimed is:

1. An amidine derivative and a pharmaceutically acceptable acid addition salt thereof, said amidine derivative being represented by the formula (I)

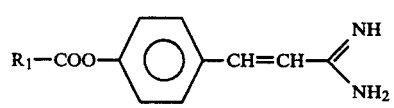

(I)

wherein

R$_1$ represents a straight or branched chain alkyl group of 1 to 6 carbon atoms, a straight or branched chain alkenyl group possessing 1 to 3 double bonds of 2 to 6 carbon atoms, a cycloalkyl group of 3 to 6 carbon atoms, a cycloalkenyl group possessing 1 to 2 double bonds of 3 to 6 carbon atoms, R$_2$—(CH$_2$)$_a$—,

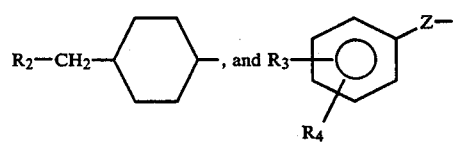

where a is 1, 2, 3, 4, 5 or 6;

R$_2$ is an amino group or guanidino group, or amino group or guanidino group possessing amino or guanidino protecting group selected from the group consisting of t-butyloxycarbonyl, benzyloxycarbonyl, acetyl, benzoyl, tosyl and nitro groups;

R$_3$ and R$_4$, which may the same or different, represent each a hydrogen atom, straight or branched chain alkyl group of 1 to 4 carbon atoms,

—O—R$_5$, —S—R$_5$, —COOR$_5$, —COR$_6$, —O—COR$_7$,

-continued

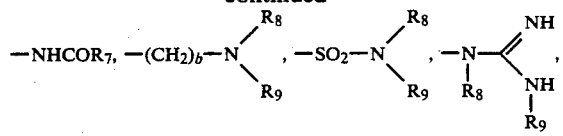

NO₂, CN, halogen, CF₃, or methylenedioxy, where b is 0, 1 or 2;

$R_5$ is a hydrogen atom, a straight or branched chain alkyl group of 1 to 4 carbon atoms, or benzyl group;

$R_6$ is a hydrogen atom or a straight or branched chain alkyl group of 1 to 4 carbon atoms;

$R_7$ is a straight or branched chain alkyl group of 1 to 4 carbon atoms;

$R_8$ and $R_9$, which may be the same or different, are each a hydrogen atom, a straight or branched chain alkyl group of 1 to 4 carbon atoms, or amino protecting group selected from the group consisting of t-butyloxycarbonyl, benzyloxycarbonyl, acetyl, benzoyl, tosyl and nitro groups;

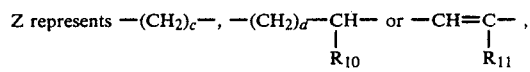

where c is 0, 1, 2 or 3, d is 0, 1 or 2;

$R_{10}$ is a straight or branched chain alkyl group of 1 to 4 carbon atoms; and $R_{11}$ is a hydrogen atom or a straight or branched chain alkyl group of 1 to 4 carbon atoms.

2. An amidino compound and a pharmaceutically acceptable acid addition salt thereof according to claim 1, wherein Z is —(CH₂)$_c$— and c is 0, 1, 2 or 3.

3. An amidino compound and a pharmaceutically acceptable acid addition salt thereof according to claim 2, wherein c is 0.

4. An amidino compound and a pharmaceutically acceptable acid addition salt thereof according to claim 1, wherein Z is

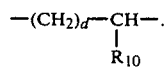

5. An amidino compound and a pharmaceutically acceptable acid addition salt thereof according to claim 1, wherein

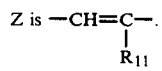

6. An amidino compound and a pharmaceutically acceptable acid addition salt thereof according to claim 3, wherein $R_3$ is

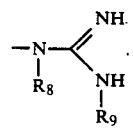

7. An amidino compound and a pharmaceutically acceptable acid addition salt thereof according to claim 3, wherein $R_3$ is

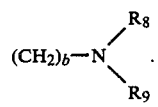

8. 4-(β-Amidinoethenyl)phenyl 4-guanidinobenzoate and a pharmaceutically acceptable acid addition salt thereof.

9. 4-(β-Amidinoethenyl)phenyl 4-aminomethylbenzoate and a pharmaceutically acceptable acid additon salt thereof.

10. An amidine derivative and a pharmaceutically acceptable acid addition salt thereof, said amidine derivative being represented by the formula (I)

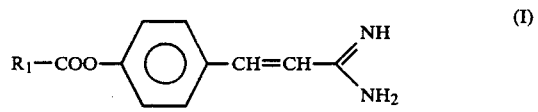

wherein $R_1$ represents a straight or branched chain alkyl group of 1 to 6 carbon atoms, a straight or branched chain alkenyl group possessing 1 to 3 double bonds of 2 to 6 carbon atoms, a cycloalkyl group of 3 to 6 carbon atoms, a cycloalkenyl group possessing 1 to 2 double bonds of 3 to 6 carbon atoms, $R_2$—(CH₂)$_a$—,

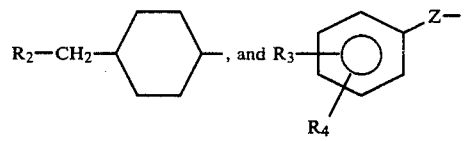

where a is 1, 2, 3, 4, 5 or 6;

$R_2$ is an amino or guanidino group which is optionally protected by a benzyloxycarbonyl group;

$R_3$ and $R_4$, which may be the same or different, represent each a hydrogen atom, straight or branched chain alkyl group of 1 to 4 carbon atoms,

—O—R₅, —S—R₅, —COOR₅, —COR₆, —O—COR₇,

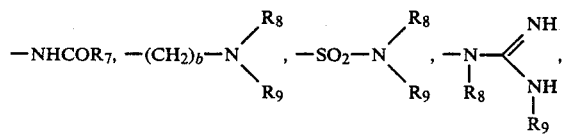

NO₂, CN, halogen, CF₃ or methylenedioxy, where b is 0, 1 or 2;

$R_5$ is a hydrogen atom, a straight or branched chain alkyl group of 1 to 4 carbon atoms, or benzyl group;

$R_6$ is a hydrogen atom or a straight or branched chain alkyl group of 1 to 4 carbon atoms;

$R_7$ is a straight or branched chain alkyl group of 1 to 4 carbon atoms;

$R_8$ and $R_9$, which may be the same or different, are each a hydrogen atom, a straight or branched chain alkyl group of 1 to 4 carbon atoms, or a benzyloxycarbonyl group;

Z represents 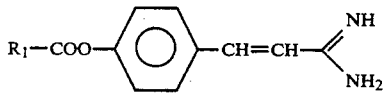

where c is 0, 1, 2 or 3, d is 0, 1 or 2;

$R_{10}$ is a straight or branched chain alkyl group of 1 to 4 carbon atoms; and $R_{11}$ is a hydrogen atom or a straight or branched chain alkyl group of 1 to 4 carbon atoms.

11. An anti-complement agent comprising as active ingredient an amidine derivative or a pharmaceutically acceptable acid addition salt thereof, said amidine derivative being represented by the formula (I)

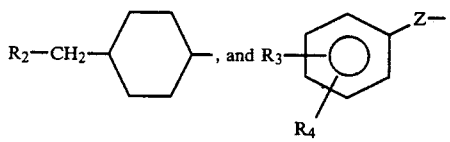 (I)

wherein $R_1$ represents a straight or branched chain alkyl group of 1 to 6 carbon atoms, a straight or branched chain alkenyl group possessing 1 to 3 double bonds of 2 to 6 carbon atoms, a cycloalkyl group of 3 to 6 carbon atoms, a cycloalkenyl group possessing 1 to 2 double bonds of 3 to 6 carbon atoms, $R_2$—(CH$_2$)$_a$—,

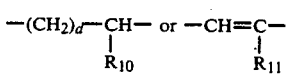

where a is 1, 2, 3, 4, 5 or 6;

$R_2$ is an amino group or guanidino group, or amino group or guanidino group possessing amino or guanidino protecting group selected from the group consisting of t-butyloxycarbonyl, benzyloxycarbonyl, acetyl, benzoyl, tosyl and nitro;

$R_3$ and $R_4$, which may be the same or different, represent each a hydrogen atom, straight or branched chain alkyl group of 1 to 4 carbon atoms,

—O—$R_5$, —S—$R_5$, —COOR$_5$—, —COR$_6$, —O—COR$_7$,

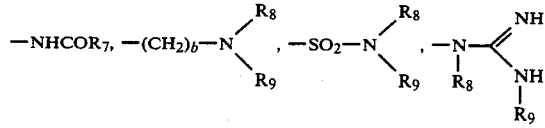

NO$_2$, CN, halogen, CF$_3$, or methylenedioxy, where b is 0, 1 or 2;

$R_5$ is a hydrogen atom, a straight or branched chain alkyl group of 1 to 4 carbon atoms, or benzyl group;

$R_6$ is a hydrogen atom or a straight or branched chain alkyl group of 1 to 4 carbon atoms;

$R_7$ is a straight or branched chain alkyl group of 1 to 4 carbon atoms;

$R_8$ and $R_9$, which may be the same or different, are each a hydrogen atom, a straight or branched chain alkyl group of 1 to 4 carbon atoms, or a benzyloxycarbonyl group;

Z represents —(CH$_2$)$_c$—, $$-(CH_2)_d-\underset{R_{10}}{CH}- \text{ or } -CH=\underset{R_{11}}{C}-$$

where c is 0, 1, 2, or 3, d is 0, 1 or 2;

$R_{10}$ is a straight or branched chain alkyl group of 1 to 4 carbon atoms; and $R_{11}$ is a hydrogen atom or a straight or branched chain alkyl group of 1 to 4 carbon atoms.

* * * * *